United States Patent [19]

Senoo et al.

[11] Patent Number: 5,238,765
[45] Date of Patent: Aug. 24, 1993

[54] ELECTROPHOTOGRAPHIC PHOTOSENSITIVE MEMBER

[75] Inventors: Akihiro Senoo; Tetsuro Kanemaru, both of Tokyo; Masakazu Matsumoto, Yokohama, all of Japan

[73] Assignee: Canon Kabushiki Kaisha, Tokyo, Japan

[21] Appl. No.: 676,444

[22] Filed: Mar. 28, 1991

[30] Foreign Application Priority Data

Mar. 30, 1990 [JP] Japan ................................ 2-80799

[51] Int. Cl.$^5$ ............................................. G03G 5/09
[52] U.S. Cl. ........................................ 430/73; 430/58; 430/59
[58] Field of Search ............... 430/58, 59, 76, 78, 430/83, 73

[56] References Cited

U.S. PATENT DOCUMENTS

| | | | |
|---|---|---|---|
| 4,450,218 | 5/1984 | Takei et al. | 430/59 |
| 4,725,518 | 2/1988 | Carmichael et al. | 430/58 |
| 4,853,308 | 8/1989 | Ong et al. | 430/59 |
| 4,931,371 | 6/1990 | Matsumoto et al. | 430/59 |
| 5,049,464 | 9/1991 | Kanemaru et al. | 430/59 |
| 5,079,118 | 1/1992 | Kikuchi et al. | 430/59 |
| 5,098,809 | 3/1992 | Kikuchi et al. | 430/73 |

FOREIGN PATENT DOCUMENTS

| | | |
|---|---|---|
| 52-4188 | 2/1977 | Japan . |
| 54-151955 | 11/1979 | Japan . |
| 55-42380 | 10/1980 | Japan . |
| 58-198043 | 11/1983 | Japan . |
| 61-132955 | 6/1986 | Japan . |
| 62-208054 | 9/1987 | Japan .................... 430/59 |

*Primary Examiner*—Marion E. McCamish
*Assistant Examiner*—Rosemary Ashton
*Attorney, Agent, or Firm*—Fitzpatrick, Cella, Harper & Scinto

[57] ABSTRACT

An electrophotographic photosensitive member with stable potential characteristics even after repeated use, comprises an electroconductive support and a photosensitive layer formed on the electroconductive support, and that photosensitive layer contains a compound represented by the general formula (1) below:

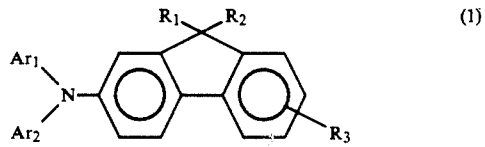

(1)

9 Claims, 1 Drawing Sheet

ELECTROPHOTOGRAPHIC PHOTOSENSITIVE MEMBER

BACKGROUND OF THE INVENTION

1. Field of the Invention

The present invention relates to an electrophotographic photosensitive member, more particularly to an electrophotographic photosensitive member having improved electrophotographic characteristics.

2. Related Background Art

An electrophotographic photosensitive member of a separate-function type, which comprises different substances each bearing a charge-generating function or a charge-transporting function, has brought about remarkable improvements in sensitivity and durability which had been disadvantages of conventional organic photosensitive members.

Such a separate-function type of electrophotographic photosensitive member is advantageous because the substances for the charge-generating material and the charge-transporting material can be selected respectively from a wide range of substances, which allows easier production of an electrophotographic photosensitive member having desired properties at low cost.

Known charge-transporting materials include pyrazolines as disclosed in Japanese Patent Publication No. 52-4188, hydrazones as disclosed in Japanese Patent Publication Nos. 55-42380 and 55-52063, triphenylamines as disclosed in Japanese Patent Publication 58-32372 and Japanese Patent Application Laid-Open No. 61-132955, and stilbenes as disclosed in Japanese Patent Application Laid-Open Nos. 54-151955 and 58-198043.

Such charge-transporting materials are required (1) to be stable to light and heat, (2) to be stable to ozone, $NO_x$, and nitric acid which are formed by corona discharge, (3) to have high ability for transporting changes, (4) to have high compatibility with organic solvents and binders, (5) to be produced readily at low cost, and so forth.

Owing to further speed-up and higher quality of images accomplished in recent years, charge-transporting materials are required to satisfy the above requirements at a higher level.

SUMMARY OF THE INVENTION

An object of the present invention is to provide an electrophotographic photosensitive member having stable potential characteristics of high sensitivity even after repeated use.

Another aspect of the present invention is to provide an electrophotographic photosensitive member having a photosensitive layer containing a compound which is readily producible at a low cost.

According to an aspect of the present invention, there is provided an electrophotographic photosensitive member comprising an electroconductive support and a photosensitive layer formed on the electroconductive support, the photosensitive layer containing a compound represented by the general formula (1):

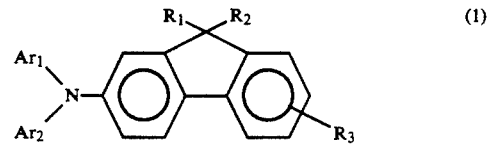

wherein $Ar_1$ and $Ar_2$ are aryl groups which may be substituted, and at least one of $Ar_1$ and $Ar_2$ is a condensed ring group; $R_1$ and $R_2$ are selected from the group consisting of hydrogen, substituted or unsubstituted alkyl groups, substituted or unsubstituted aralkyl group and substituted or unsubstituted aryl groups; and $R_3$ is selected from the group consisting of hydrogen, substituted or unsubstituted alkyl groups, substituted or unsubstituted alkoxy groups and halogens.

DESCRIPTION OF THE PREFERRED EMBODIMENT

Figure 1:
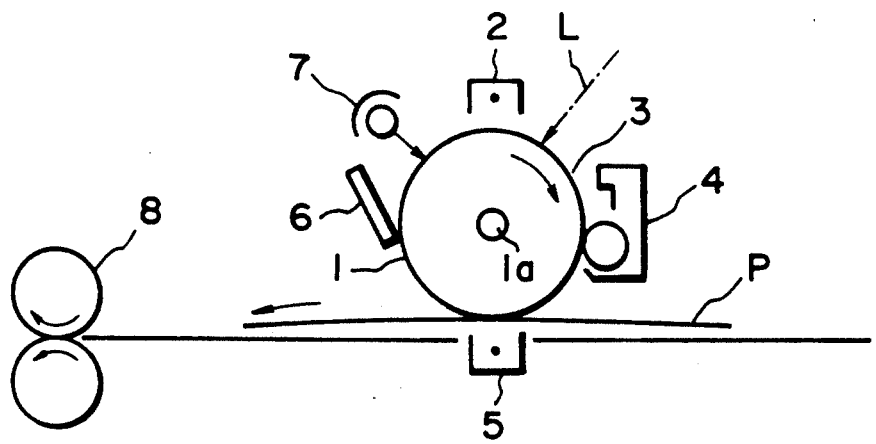
FIG. 1 illustrates an outline of constitution of an electrophotographic apparatus employing the electrophotographic photosensitive member of the present invention.

The photosensitive layer constituting the electrophotographic photosensitive member of the present invention contains a compound represented by the general formula (1) below:

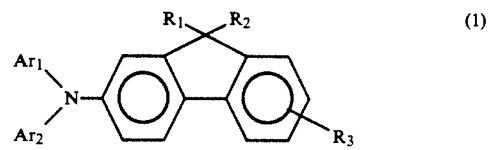

wherein $Ar_1$ and $Ar_2$ are aryl groups which may be substituted, and at least one of $Ar_1$ and $Ar_2$ is a condensed ring group; $R_1$ and $R_2$ are selected from the group consisting of hydrogen, substituted or unsubstituted alkyl groups, substituted or unsubstituted aralkyl group and substituted or unsubstituted aryl groups; and $R_3$ is selected from the group consisting of hydrogen, substituted or unsubstituted alkyl groups, substituted or unsubstituted alkoxy groups and halogens.

The aryl group includes phenyl, biphenyl, naphthyl, anthryl, and the like, and the condensed ring group includes naphthyl, anthryl, phenanthryl, pyrenyl, and the like. The alkyl group includes methyl, ethyl, propyl, isopropyl, and the like. The aralkyl group includes benzyl, phenethyl, and the like. The alkoxy group includes methoxy, ethoxy, propoxy, and the like. The halogen includes fluorine, chlorine, bromine, and the like.

The substituent which may be incorporated in the aforementioned groups includes the above-mentioned alkyl, alkoxy, halogen, and the like.

Preferably in the present invention, one of $Ar_1$ and $Ar_2$ is substituted or unsubstituted phenyl, and the other one thereof is a condensed ring group. More preferably, one of $Ar_1$ and $Ar_2$ is phenyl, and the other one is naphthyl.

Specific examples of the compounds which are useful in the present invention are shown below. The present invention is not limited at all by these compounds.
Exemplified compounds (1) to (27) [Formulas]
(1)
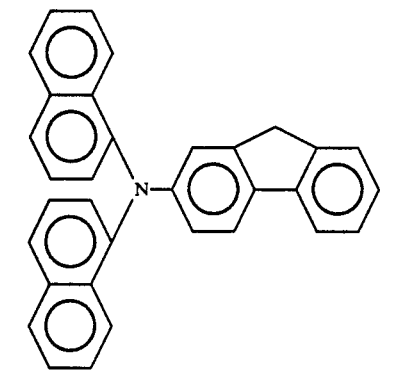
(2)
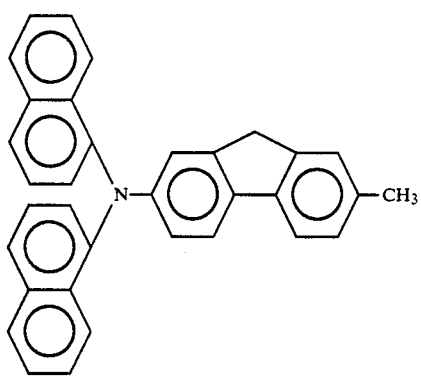
(3)
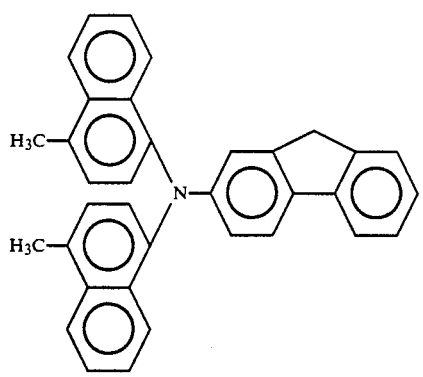
(4)
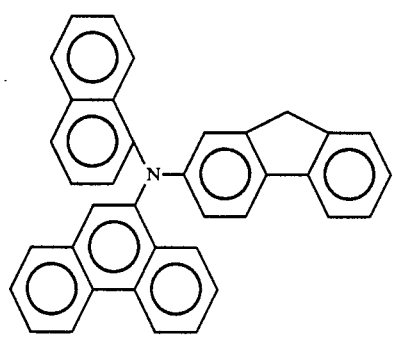
-continued
(5)
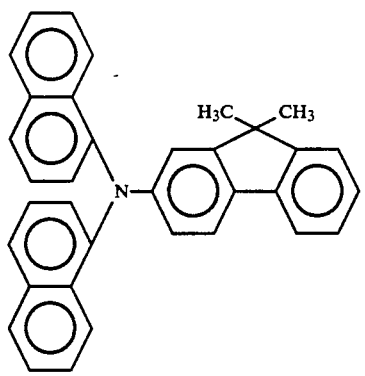
(6)
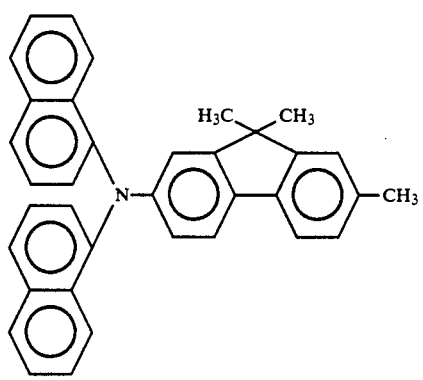
(7)
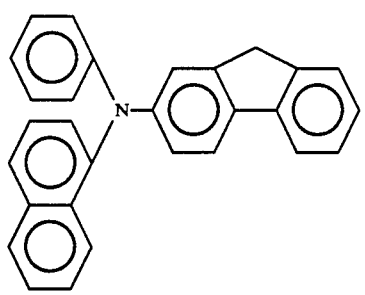
(8)
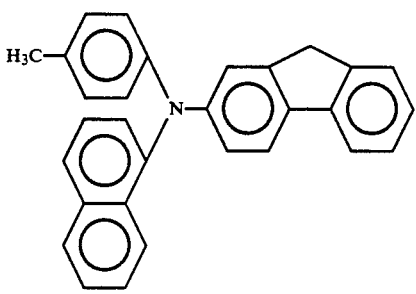

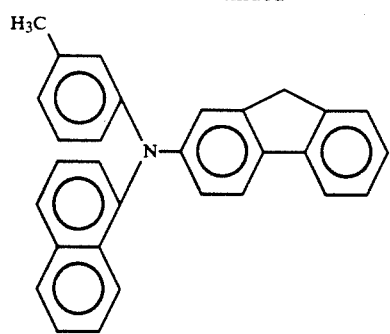 (9)
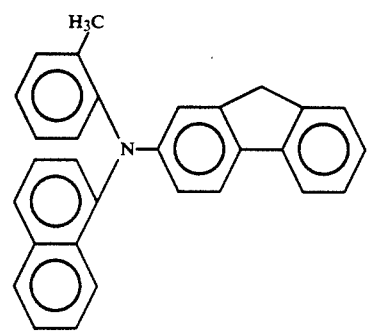 (10)
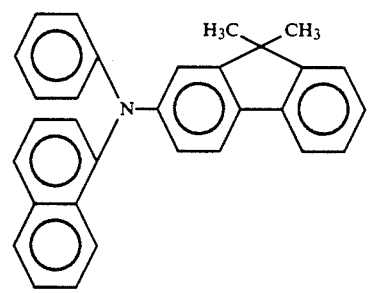 (11)
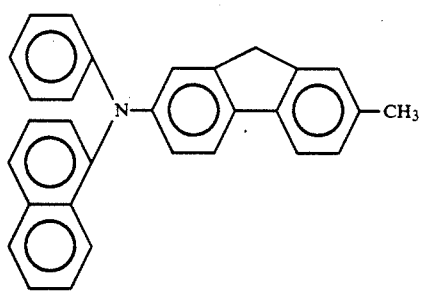 (12)
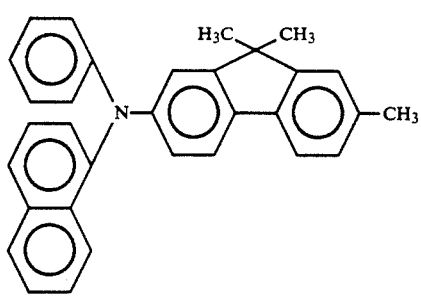 (13)
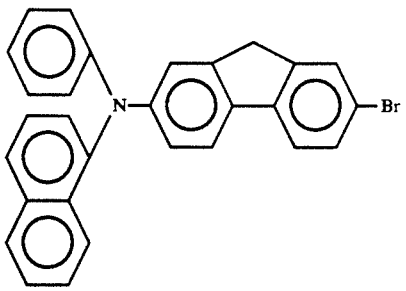 (14)
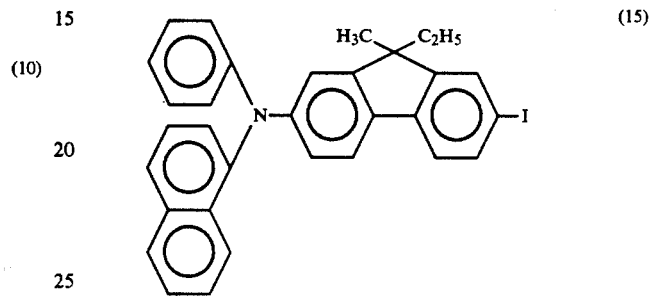 (15)
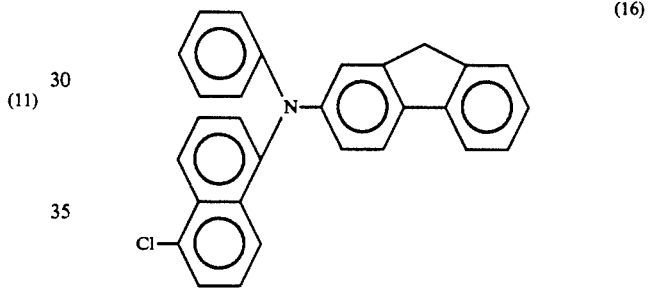 (16)
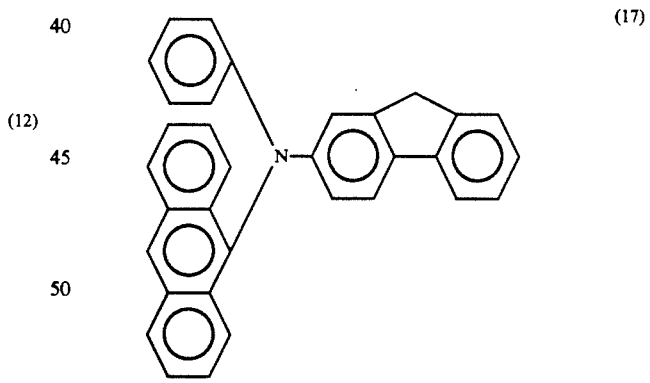 (17)
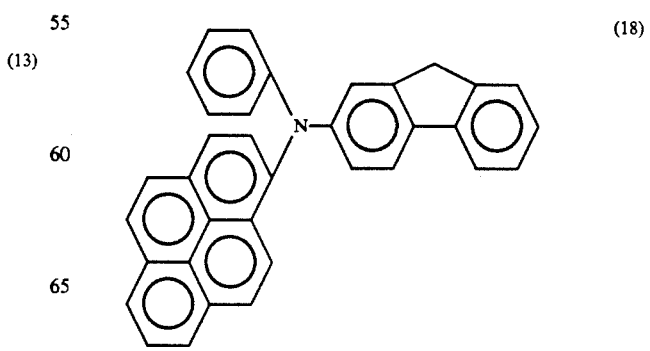 (18)

-continued
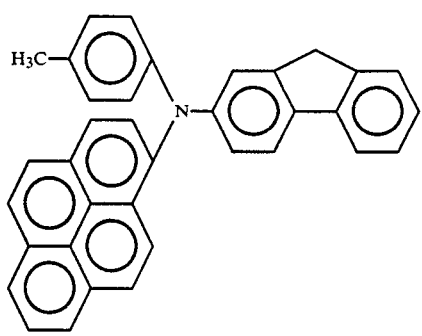 (19)
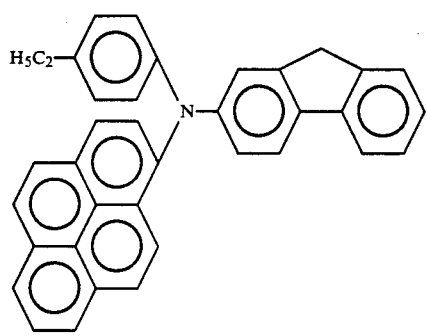 (20)
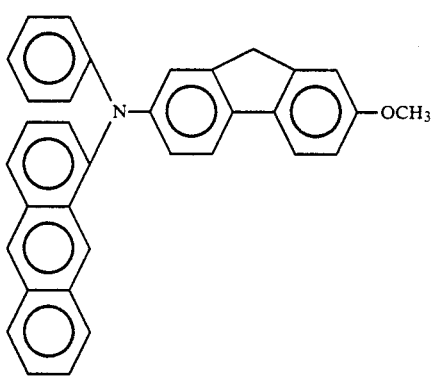 (21)
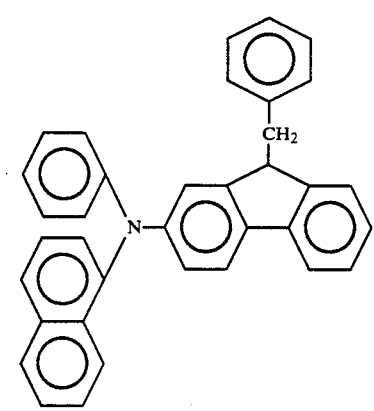 (22)
-continued
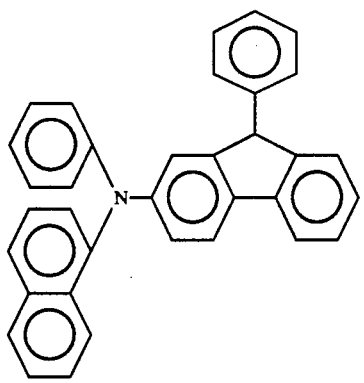 (23)
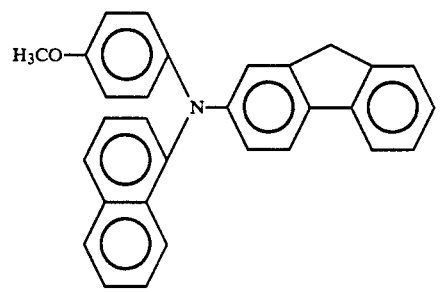 (24)
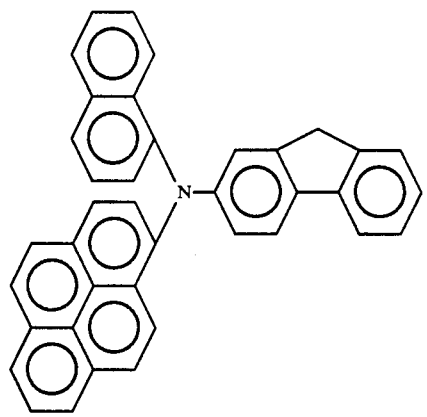 (25)
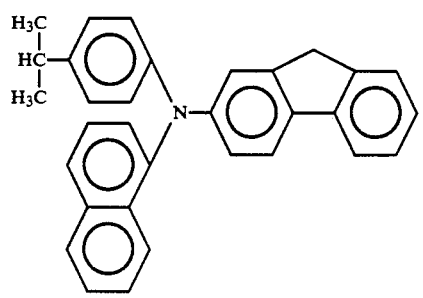 (26)

-continued

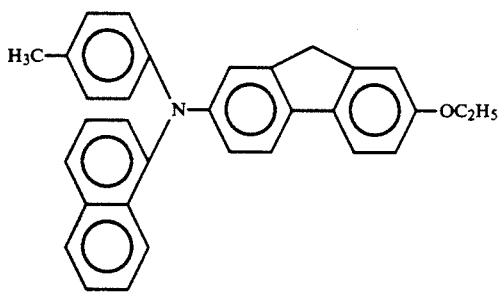
(27)

The compound represented by Formula (1) employed in the present invention can be synthesized by reacting a secondary amine represented by the general formula (2)

(2)

(where $Ar_1$ and $Ar_2$ are the same as mentioned above) with an iodofluorene represented by the formula (3) below:

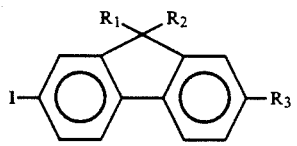
(3)

(where $R_1$, $R_2$, and $R_3$ are the same as mentioned above) in the presence of anhydrous potassium carbonate and powdery copper using orthodichlorobenzene as the solvent under reflux, and subsequently separating and purifying the resulting crude reaction product by means of a silica gel column.

However, the method of synthesis of the compound of the present invention is not limited to the above-mentioned method.

The electrophotographic photosensitive member of the present invention comprises a photosensitive layer laid on an electroconductive support. The constitution of the photosensitive layer includes the types as shown below. In the types (1), (2), and (4), the layers are shown in the order of (Lower layer)/(Upper layer).

(1) Layer containing a charge-generating substance/-layer containing a charge transporting substance, (2) Layer containing a charge transporting substance/layer containing a charge-generating substance, (3) Layer containing a charge-generating substance and a charge-transporting substance, (4) Layer containing a charge-generating substance/-layer containing a charge-generating substance and a charge-transporting substance.

The fluorene represented by the general formula (1) has a high ability for enhancing the mobility of positive holes. In the type (1) of photosensitive layer, the compound is preferably employed for negative charges; in type (2) the compound is preferably employed for positive charges; and in types (3) and (4), the compound may be employed either for positive charges and for negative charges.

Naturally the constitution of the electrophotographic photosensitive member of the present invention is not limited to the above-mentioned fundamental constitution.

The particularly preferable type of the photosensitive layers of the present invention are those of the type (1), and described in detail.

The charge-generating substance in the present invention may be any substance if it has charge-generating ability. The examples of the charge-generating substance are as below:

(1) Azo pigments including monoazo, bisazo, and trisazo, (2) Phthalocyanine pigments including metal phthalocyanine, and non-metal phthalocyanine, (3) Indigo pigments including indigo and thioindigo, (4) Perylene pigments including perylenic anhydride and perylenic imide, (5) Polycyclic quinone pigments including anthraquinone and pyrenequinone, (6) Squarilium dyes, (7) Pyrylium salts and thiopyrylium salts, (8) Triphenylmethane dyes, and (9) Inorganic substances including selenium, and amorphous silicon.

Such a charge-generating material may be used singly or in combination of two or more thereof.

A layer containing a charge-generating substance, namely a charge-generating layer can be formed by dispersing the charge-generating substance in an appropriate binder and applying the resulting dispersion on an electroconductive support. It can also be formed by forming a thin film on an electroconductive support by a dry method such as vapor deposition, sputtering, CVD, and the like.

The above-mentioned binder may be selected from a great variety of binder resins including polycarbonates, polyesters, polyarylates, butyral resins, polystyrenes, polyvinylacetals, diallyl phthalate resins, acrylic resins, methacrylic resins, vinyl acetate resins, phenol resins, silicone resins, polysulfones, styrene-butadiene copolymers, alkid resins, epoxy resins, urea resins, vinyl chloridevinyl acetate copolymers, and the like. However, the binder is not limited thereto.

These resins may be used singly or in combination of two or more thereof.

The resin is contained in the charge-generating layer in an amount preferably of not more than 80% by weight, more preferably not more than 40% by weight of the total layer.

The film thickness of the charge-generating layer is preferably not more than 5 μm, more preferably in the range of from 0.01 μm to 2 μm.

The charge-generating layer may further contain a sensitizing agent.

The layer containing a charge-transporting substance, namely a charge-transporting layer can be formed by combining the fluorene compounds represented by the formula (1) with an appropriate binder resin. In the present invention, another charge-transporting substance may further be used in combination.

The binder resin for the charge-transporting layer includes photoconductive polymers such as polyvinylcarbazoles, polyvinylanthracenes and the like in addition to the aforementioned substances used as the binder for the charge-generating layer.

The fluorene represented by the formula (1) is mixed with the binder preferably in an amount of from 10 to 500 parts by weight for 100 parts by weight of the binder.

The film thickness of the charge-transporting layer is preferably in the range of from 5 μm to 40 μm, more preferably from 10 μm to 30 μm.

The charge-transporting layer may additionally contain an antioxidant, an ultraviolet absorbing agent, a plasticizer, or a known charge-transporting substance, if necessary.

In the case where the photosensitive layer has the constitution (3) mentioned above, namely a single layer constitution, the layer is formed by dispersing the aforementioned charge-generating substance and the compound of formula (1) are dispersed or dissolved to prepare a coating liquid, applying the coating liquid on a support, and drying it. The thickness of the film is preferably in the range of from 5 μm to 40 μm, more preferably from 10 μm to 30 μm.

Between the electroconductive support and the photosensitive layer, a layer having both a barrier function and an adhesion function, namely a subbing layer, may be provided in the present invention.

The material for the subbing layer includes polyvinyl alcohol, polyethylene oxide, ethylcellulose, methylcellulose, casein, polyamides, glue, gelatin, and the like.

The subbing layer can be formed by dissolving the above material in an appropriate solvent and applying the resulting solution on an electroconductive support. The film thickness is preferably not more than 5 μm, more preferably in the range of from 0.2 μm to 3.0 μm.

Further, for protecting the photosensitive layer from various external mechanical and electrical forces, a resin layer or a resin layer containing an electroconductive substance dispersed therein may be provided on the photosensitive layer in the present invention.

The layers mentioned above can be formed on an electroconductive support by coating such as immersion coating, spray coating, spinner coating, roller coating, Meyer-bar coating, and blade coating.

The electroconductive support in the present invention includes those of the types shown below (1) A metal such as aluminum, an aluminum alloy, stainless steel, copper, and the like in a plate shape or a drum shape.

(2) A non-electroconductive support such as glass, a resin, and paper or an electroconductive support, as mentioned in the above item (1), which has a film formed thereon by vapor deposition or laminating a metal such as aluminum, palladium, rhodium, gold, platinum, and the like.

(3) A non-electroconductive support such as glass, a resin, and paper or an electroconductive support, as mentioned in the above item (1), which has a layer formed thereon by vapor deposition of coating of an electroconductive polymer, or an electroconductive compound such as tin oxide, indium oxide, and the like.

The electrophotographic photosensitive member of the present invention is not only useful for electrophotographic copying machines but also useful for a variety of application field of electrophotography such as laser printers, CRT printers, electrophotographic engraving systems, and the like.

FIG. 1 shows a schematic diagram of a usual transfer type electrophotographic apparatus employing the electrophotographic photosensitive member of the present invention.

In FIG. 1, a drum type photosensitive member 1 serves as an image carrier, being driven to rotate around the axis 1a in the arrow direction at a predetermined peripheral speed. The photosensitive member 1 is uniformly charged, positively or negatively, at the peripheral face by an electrostatic charging means 2 during the rotation, and then exposed to image-exposure light L (e.g. slit exposure, laser beam-scanning exposure, etc.) at the exposure part 3 with an image-exposure means (not shown in the figure), whereby electrostatic latent images are sequentially formed on the peripheral surface in accordance with the exposed image.

The electrostatic latent image is developed with a toner by a developing means 4, and the toner-developed images are sequentially transferred by a transfer means 5 onto a transfer-receiving material P which is fed between the photosensitive member 1 and the transfer means 5 synchronized with the rotation of the photosensitive member 1, from a transfer-receiving material feeder which is not shown in the figure.

The transfer-receiving material P having received the transferred image is separated from the photosensitive member surface, and introduced to an image fixing means 8 for fixation of the image and discharged from the copying machine as a duplicate copy.

The surface of the photosensitive member 1, after the image transfer, is cleaned with a cleaning means 6 to remove the residual non-transferred toner if any, and is treated for electrostatic charge eliminating means 7 for repeated use for image formation.

The generally and usually employed charging means 2 for uniformly charging the photosensitive member 1 is a corona charging apparatus. The generally and usually employed transfer means 5 is also a corona charging means. In the electrophotographic apparatus, two or more of the constitutional elements of the above described photosensitive member, the developing means, the cleaning means, etc. may be integrated as one apparatus unit, which may be removable from the main body of the apparatus. For example, at least one of an electrostatic charging means, a developing means, and a cleaning means is combined with the photosensitive member into one unit removable from the main body of the apparatus by aid of a guiding means such as rails of the main body of the apparatus. A electrostatic charging means and/or a developing means may be combined with the aforementioned unit.

In the case where the electrophotographic apparatus is used as a copying machine or a printer, the optical image exposure light L is projected onto the photosensitive member as the reflected light or transmitted light from an original copy, or otherwise the signalized information is read out by a sensor from an original copy and then followed by scanning with a laser beam, driving an LED array, or driving a liquid crystal shutter array according to the signal, the exposure light is projected onto a photosensitive member.

Figure 2:
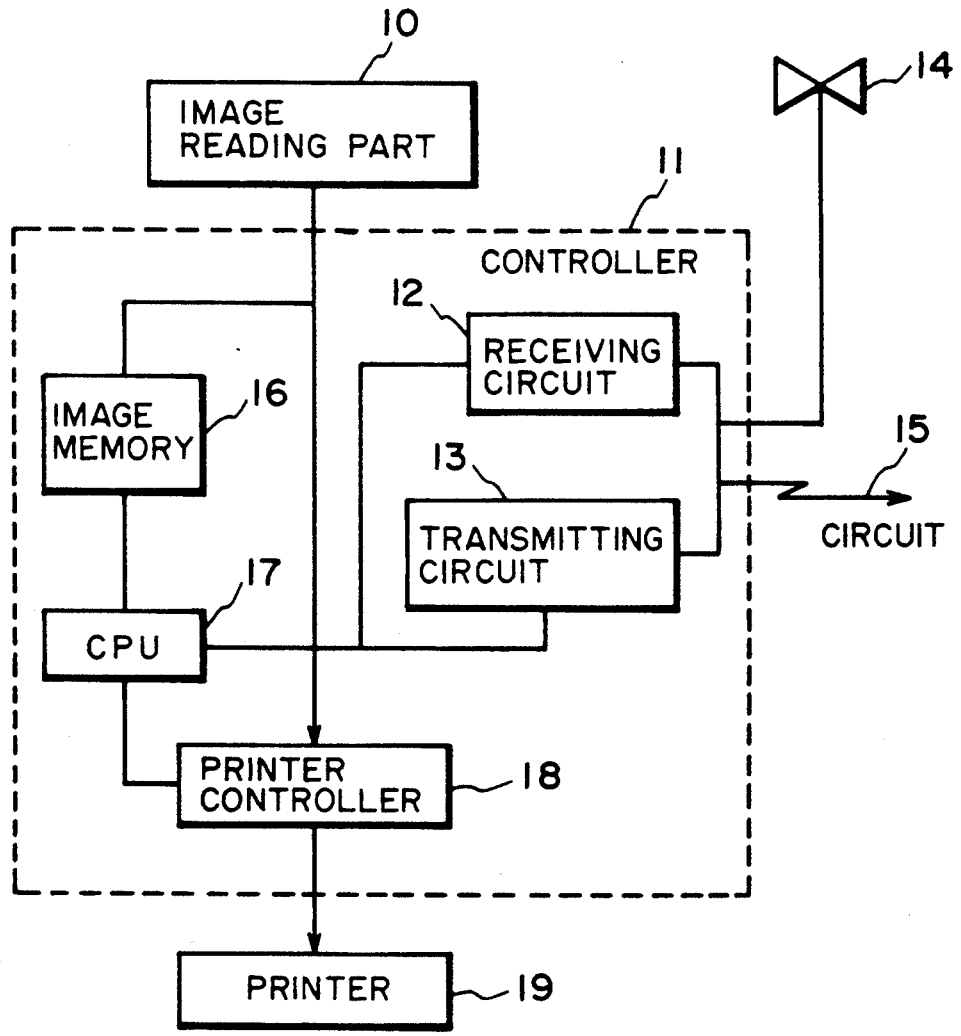
FIG. 2 illustrates an example of a block diagram of a facsimile employing the electrophotographic photosensitive member of the present invention.

In the case where the electrophotographic apparatus is used as a printer of a facsimile apparatus, the optical image exposure light L is for printing the received data. FIG. 2 is a block diagram of an example of this case.

A controller 11 controls an image reading part 10 and a printer 19. The whole of the controller 11 is controlled by a CPU 17. Readout data from the image reading part is transmitted through a transmitting circuit 13 to the other communication station. Data received from the other communication station is transmitted through a receiving circuit 12 to a printer 19. The image data is stored in image memory. A printer controller 18 controls a printer 19. The numeral 14 denotes a telephone set.

The image received through the circuit 15, namely image information from a remote terminal connected through the circuit, is demodulated by receiving circuit 12, treated for decoding of the image information in CPU 17, and successively stored in image memory 16. When at lest one page of the image has been stored in the image memory 16, the image is recorded in such a manner that the CPU 17 reads out the one page of image information, and send out the decoded one page of information to the printer controller 18, the controller controls the printer 19 on receiving the one page of information from CPU 17 to record the image information.

Incidentally the CPU 17 receives the following page of information while recording is conducted by the printer 19.

Images are received and recorded in the manner as described above.

EXAMPLE 1

The bisazo pigment 5.0 g, represented by the formula below, was dispersed in a solution of 2.0 g of a butyral resin (butyralation degree: 63 mol %) in 100 ml of cyclohexanone using a sand mill for 24 hours to prepare a coating liquid.

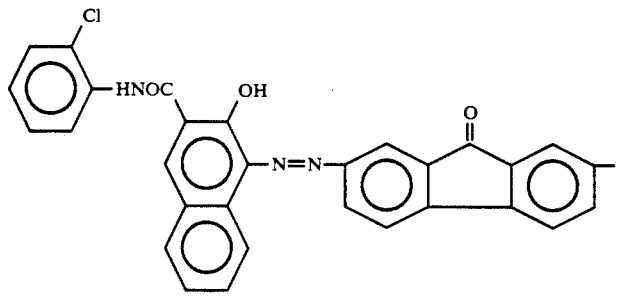

This coating liquid was applied onto an aluminum sheet with a Meyer bar to form a charge-generating-layer of 0.5 μm in thickness after dried.

Separately, 10 g of Exemplified compound (8) as a charge-transporting substance and 10 g of polycarbonate (weight-average molecular weight: 20,000) were dissolved in 70 g of chlorobenzene. This solution was applied onto the aforementioned charge-generating layer with a Meyer bar to form a charge-transporting layer of 20 μm in dry thickness, thereby an electrophotographic photosensitive member was prepared.

The electrophotographic photosensitive member thus prepared was evaluated for charging characteristics by an electrostatic copying-paper tester (Model SP-428, made by Kawaguchi Denki K.K.) in such a manner that the the photosensitive member was charged by corona discharge of −5 KV by a static mode, left standing for 1 second in the dark for dark decay, and exposed to the light of illuminance of 20 lux.

The charging characteristics measured were the surface potential ($V_0$) immediately after the charging, and the quantity of light exposure required to reduce the surface potential after the one second dark decay ($V_1$) to a 1/5 level ($E_{1/5}$).

For measuring the change of the light-portion potential and the dark-portion potential in repeated use, the prepared photosensitive member was attached onto a photosensitive drum of a PPC copying machine (NP-3825, made by Canon K.K.), and was subjected to 10,000-sheet copying. Thus the change of the light-portion potential ($V_L$) and the dark-portion potential ($V_D$) during the time of 10,000-sheet copying were measured.

The $V_D$ and $V_L$ at the initial stage were set respectively to −700 V and −200 V. The results were as shown below:

$V_0$: −703 V
$V_1$: −697 V
$E_{1/5}$: 1.1 lux.sec
Initial potential
$V_D$: −700 V
$V_L$: −200 V
Potential after 10,000-sheet copying
$V_D$: −697 V
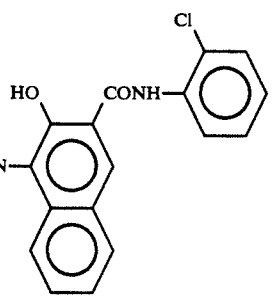
$V_L$: −205 V

EXAMPLES 2-10

Electrophotographic photosensitive members of Examples 2 to 10 were prepared in the same manner as in Example 1 except that Exemplified compounds (1), (2), (5), (7), (9), (15), (20), (22), and (24) were employed respectively instead of the Exemplified compound (8), and the pigment having the structure below was employed as a charge-generating substance.

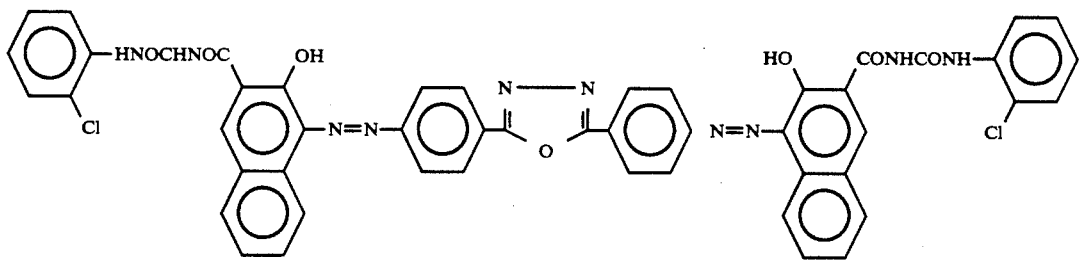

The electrophotographic properties of the respective photosensitive members were evaluated in the same manner as in Example 1. The results are shown in Table 1 and Table 2.

TABLE 1

| Example | Exemplified compound | $V_0$ (−V) | $V_1$ (−V) | $E_{1/5}$ (lux.sec) |
|---|---|---|---|---|
| 2 | (1) | 703 | 700 | 1.9 |
| 3 | (2) | 697 | 696 | 1.7 |
| 4 | (5) | 699 | 695 | 2.1 |
| 5 | (7) | 699 | 697 | 1.1 |
| 6 | (9) | 695 | 690 | 1.2 |
| 7 | (15) | 701 | 697 | 1.5 |
| 8 | (20) | 697 | 695 | 2.3 |
| 9 | (22) | 700 | 695 | 1.4 |
| 10 | (24) | 703 | 693 | 1.3 |

TABLE 2

| Example | Initial potential $V_D$ (−V) | Initial potential $V_L$ (−V) | Potential after 10,000-sheet copying $V_D$ (−V) | Potential after 10,000-sheet copying $V_L$ (−V) |
|---|---|---|---|---|
| 2 | 700 | 200 | 691 | 215 |
| 3 | 700 | 200 | 692 | 205 |
| 4 | 700 | 200 | 688 | 210 |
| 5 | 700 | 200 | 695 | 205 |
| 6 | 700 | 200 | 690 | 207 |
| 7 | 700 | 200 | 693 | 205 |
| 8 | 700 | 200 | 685 | 215 |
| 9 | 700 | 200 | 693 | 208 |
| 10 | 700 | 200 | 687 | 215 |

COMPARATIVE EXAMPLES 1-4

Electrophotographic photosensitive members were prepared and evaluated in the same manner as in Example 2 except that the comparative compounds below were employed instead of the Exemplified compound (2).

Comparative compound (1)

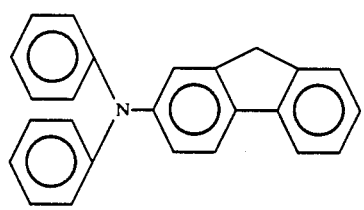

Comparative compound (2)

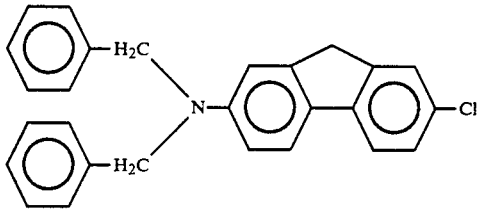

Comparative compound (3)

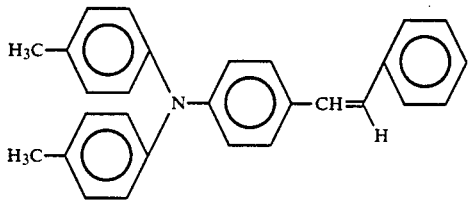

Comparative compound (4)

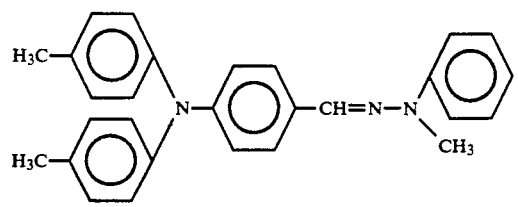

The results are shown in Table 3 and Table 4.

TABLE 3

| Comparative Example | Comparative compound | $V_0$ (−V) | $V_1$ (−V) | $E_{1/5}$ (lux.sec) |
|---|---|---|---|---|
| 1 | (1) | 695 | 690 | 4.2 |
| 2 | (2) | 703 | 685 | 5.8 |
| 3 | (3) | 698 | 690 | 4.1 |
| 4 | (4) | 685 | 650 | 3.5 |

TABLE 4

| Comparative Example | Initial potential $V_D$ (−V) | Initial potential $V_L$ (−V) | Potential after 10,000-sheet copying $V_D$ (−V) | Potential after 10,000-sheet copying $V_L$ (−V) |
|---|---|---|---|---|
| 1 | 700 | 200 | 670 | 255 |
| 2 | 700 | 200 | 630 | 450 |
| 3 | 700 | 200 | 600 | 320 |
| 4 | 700 | 200 | 590 | 270 |

EXAMPLE 11

Onto an aluminum sheet, a solution of 5 g of N-methoxymethylated 6-nylon resin (weight-average molecular weight: 32,000) and 10 g of alcohol-soluble nylon copolymer (weight-average molecular weight: 29,000) in 95 g of methanol was applied with a Meyer bar to form a subbing layer having a dry thickness of 1 μm.

Separately, 10 g of the charge-generating substance represented by the structural formula below:

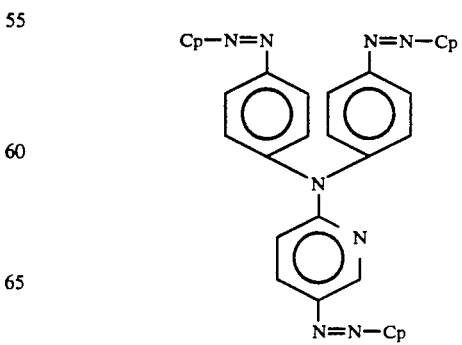

-continued

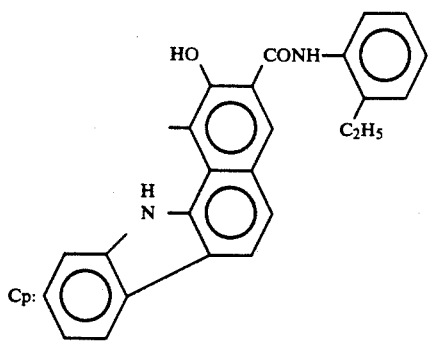

and 5 g of polyvinylbutyral (butyralation degree: 63%, weight-average molecular weight: 44,000) were dispersed in 200 g of dioxane by a ball mill for 48 hours. The resulting dispersion was applied on the aforementioned subbing layer by a blade coating method to form a charge-generating layer having a dry thickness of 0.2 μm.

Ten grams of Exemplified compound (11) and 10 g of polymethyl methacrylate (weight-average molecular weight: 50,000) were dissolved in 70 g of chlorobenzene. The resulting solution was applied onto the above-mentioned charge-generating layer by a blade coating method to form a charge-transporting layer having a dry thickness of 20 μm.

The electrophotographic photosensitive member thus prepared was subjected to corona discharge of −5 KV, and the surface potential ($V_0$) caused thereby was measured. Further, the photosensitive member was left standing in the dark for one second to undergo dark decay, and then the surface potential ($V_1$) after the dark decay was measured. The sensitivity was evaluated by measurement of the quantity of light exposure for reducing the potential after the dark decay ($V_1$) to 1/6 level ($E_{1/6}$: μJ/cm$^2$). The light source employed was a ternary semiconductor laser of gallium/aluminum/arsenic (output power: 5 mW, wavelength: 780 nm).

The results were as below.
$V_0$: −700 V, $V_1$: −695 V
$E_{1/6}$: 0.85 μJ/cm$^2$ The above photosensitive member was mounted to a laser beam printer (LBP-CX, made by Canon K.K.) which is an electrophotographic printer of reversal development type equipped with the aforementioned semiconductor laser, and was subjected to a practical image forming test under the conditions below.

Surface potential after primary charge: −700 V
Surface potential after image exposure: −150 V (quantity of exposure: 2.0 μJ/cm$^2$)
Polarity of developement: negative
Process speed: 50 mm/sec
Developing condition (developing bias): −450 V
Type of scanning after image exposure: Image scanning
Light exposure before primary charging: 50 lux.sec, entire exposure with red light The image was formed by line-scanning of the laser beam according to letter signals and picture image signals. Both the letters and the picture images were printed satisfactorily.

Subsequently, 5000 sheets of image printing was conducted continuously. Stable and satisfactory prints were obtained from the beginning to the 5000-th sheet.

EXAMPLE 12

Oxytitanium phthalocyanine 5 g was added to a solution of 2 g of a phenoxy resin in cyclohexanone 100 g, and dispersed by means of a ball mill for 48 hours. This dispersion was applied on an aluminum sheet with a Meyer bar and dried at 80° C. for 30 minutes to form a charge-generating layer of 0.5 μm thickness.

A solution of 10 g of Exemplified compound (7) and 10 g of bisphenol Z type polycarbonate resin (weight-average molecular weight: 20,000) in 70 g chlorobenzene was prepared and was applied on the charge-generating layer prepared above using a Meyer bar, and dried at 120° C. for one hour to form a charge-transporting layer of 20 μm thickness.

The electrophotographic photosensitive member thus prepared was evaluated for charging properties in the same manner as in Example 11.

The results were as below.
$V_0$: −702 V, $V_1$: −700 V
$E_{1/6}$: 0.30 μJ/cm$^2$

EXAMPLE 13

A photosensitive member was prepared in the same manner as in Example 11 except that the charge-generating layer and the charge-transporting layer is formed in the reversed order, and the charge was made positive.

The results were as below.
$V_0$: −705 V, $V_1$: −698 V
$E_{1/6}$: 1.1 μJ/cm$^2$

EXAMPLE 14

Three grams of 4-(4-dimethylaminophenyl)-2, 6-diphenylthiapyrylium perchlorate and 5 g of Exemplified compound (11) were mixed with 100 g of a solution containing 10 g copolymeric polyester (weight-average molecular weight: 49,000) in toluene (50 parts by weight)-dioxane (50 parts by weight), and the mixture was dispersed for 6 hours by means of a ball mill. This dispersion was applied on an aluminum sheet with a Meyer bar, and dried at 100° C. for 2 hours to form a photosensitive layer of 17 μm thick.

The electrophotographic photosensitive member thus prepared was subjected to measurement of charging properties in the same manner as in Example 1.

The results were as shown below.
$V_0$: −700 V
$V_1$: −695 V
$E_{1/5}$: 3.2 lux.sec
Initial potential
$V_D$: −700 V
$V_L$: −200 V
Potential after 10,000-sheet copying
$V_D$: −690 V
$V_L$: −215 V

EXAMPLE 15

Onto an aluminum sheet, a 5% solution of alcohol soluble nylon (6-66-610-12 four-component nylon copolymer) in methanol was applied to form a subbing layer having a dry thickness of 0.5 μm.

5 g of the pigment of the structural formula below was dispersed in 95 ml of tetrahydrofuran by a sand mill.

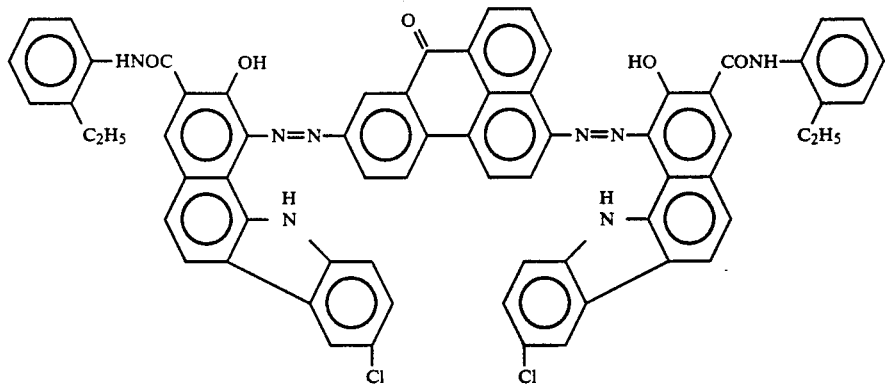

Five grams of Exemplified compound (12) and 10 g of bisphenol A type polycarbonate (weight-average molecular weight: 50,000) were dissolved in 30 g of a mixed solvent of chlorobenzene (70 parts by weight)-dichloromethane (30 parts by weight). This solution was added to the dispersion prepared above, and the mixture was further dispersed for 2 hours by means of a sand mill.

The resulting dispersion was applied on the subbing layer formed above with a Meyer bar, and dried to give a dry film thickness of 15 μm.

The electrophotographic properties of the electrophotographic photosensitive member thus prepared was measured in the same manner as in Example 11.

The results were as below.

$V_0$: −697 V, $V_1$: −690 V $E_{1/6}$: 2.7 μJ/cm$^2$

What is claimed is:

1. An electrophotographic photosensitive member comprising an electroconductive support and a photosensitive layer formed on the electroconductive support, the photosensitive layer containing a compound represented by the general formula (1) below:

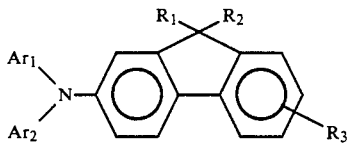

wherein Ar$_1$ and Ar$_2$ are substituted or unsubstituted phenyl or substituted or unsubstituted naphthyl, and at least one of Ar$_1$ and Ar$_2$ is substituted or unsubstituted naphthyl; R$_1$ and R$_2$ are selected from the group consisting of hydrogen, substituted or unsubstituted alkyl groups, substituted or unsubstituted aralkyl groups and substituted or unsubstituted aryl groups; and R$_3$ is selected from the group consisting of hydrogen, substituted or unsubstituted alkyl groups, substituted or unsubstituted alkoxy groups and halogens.

2. An electrophotographic photosensitive member according to claim 1, wherein one of the Ar$_1$ and Ar$_2$ is a substituted or unsubstituted phenyl, and the other one "is a substituted or unsubstituted naphthyl."

3. An electrophotographic photosensitive member according to claim 1, wherein the photosensitive layer comprises a charge-generating layer and a charge-transporting layer.

4. An electrophotographic photosensitive member according to claim 3, wherein the charge-transporting layer is overlaid on the charge-generating layer.

5. An electrophotographic photosensitive member according to claim 3, wherein the charge-generating layer is overlaid on the charge-transporting layer.

6. An electrophotographic photosensitive member according to claim 1, wherein the photosensitive layer is a single layer.

7. An electrophotographic photosensitive member according to claim 1, wherein a subbing layer is provided between the electroconductive support and the photosensitive layer.

8. An electrophotographic photosensitive member according to claim 1, wherein a protective layer is provided on the photosensitive layer.

9. An electrophotographic apparatus comprising an electrophotographic photosensitive member, a means for forming an electrostatic latent image, a means for developing the electrostatic latent image formed, and a means for transferring a developed image onto a transfer-receiving material; the electrophotographic photosensitive member comprising an electroconductive support and a photosensitive layer formed on the electroconductive support, the photosensitive layer containing a compound represented by the general formula (1) below:

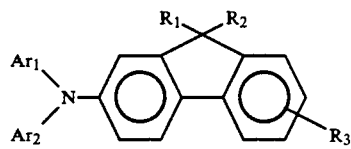

wherein Ar$_1$ and Ar$_2$ are substituted or unsubstituted phenyl or substituted or unsubstituted naphthyl, and at least one of Ar$_1$ and Ar$_2$ is substituted or unsubstituted naphthyl; R$_1$ and R$_2$ are selected from the group consisiting of hydrogen, substituted or unsubstituted alkyl groups, substituted or unsubstituted aralkyl groups and substituted or unsubstituted aryl groups; and R$_3$ is selected from the group consisting of hydrogen, substituted or unsubstituted alkyl groups, substituted or unsubstituted alkoxy groups and halogens.

* * * * *